United States Patent [19]

Ranken

[11] Patent Number: 4,547,593

[45] Date of Patent: Oct. 15, 1985

[54] PREPARATION OF (HYDROCARBYLTHIO)PHENOLS

[75] Inventor: Paul F. Ranken, Baton Rouge, La.

[73] Assignee: Ethyl Corporation, Richmond, Va.

[21] Appl. No.: 593,562

[22] Filed: Mar. 26, 1984

[51] Int. Cl.$^4$ .......................................... C07C 149/36
[52] U.S. Cl. .................................... 568/54; 549/469; 568/46; 568/47; 568/48; 568/52; 568/53
[58] Field of Search ...................... 568/54, 46, 47, 48, 568/52, 53

[56] References Cited

U.S. PATENT DOCUMENTS 2,923,743  2/1960  Delfs et al. .............................. 568/54
4,324,920  4/1982  McKinnie et al. ..................... 568/54

FOREIGN PATENT DOCUMENTS 1291191  10/1972  United Kingdom .

OTHER PUBLICATIONS

N. Onodera et al., Chem Abstracts, 74:22543j, (1971).
N. Onodera et al., Chem. Abstracts, 74:42145j, (1971).

Primary Examiner—Donald G. Daus
Assistant Examiner—Mary E. Ceperley
Attorney, Agent, or Firm—Donald L. Johnson; John F. Sieberth; Patricia J. Hogan

[57] ABSTRACT

(Hydrocarbylthio)phenols, such as 2-(alkylthio)phenols, are prepared by heating one or more (hydrocarbylthio)phenols selected from 2-, 3-, 4-, and poly(hydrocarbylthio)phenols in the presence of a catalytic amount of an aluminum phenoxide to redistribute the starting materials.

8 Claims, No Drawings

PREPARATION OF (HYDROCARBYLTHIO)PHENOLS

FIELD OF INVENTION

This invention relates to (hydrocarbylthio)phenols and more particularly to a process for preparing them by the redistribution of other (hydrocarbylthio)phenols.

BACKGROUND

As disclosed in U.S. Pat. Nos. 2,923,743 (Delfs et al.) and 4,324,920 (McKinnie et al.), it is known that 2-(hydrocarbylthio)phenols are useful as pharmaceutical and agricultural intermediates and that they can be prepared by reacting appropriate phenols with hydrocarbyl disulfides in the presence of aluminum compounds, such as the aluminum phenoxide catalyst of McKinnie et al. Unfortunately, these 2-(hydrocarbylthio)phenol syntheses also lead to the formation of significant quantities of 4-(hydrocarbylthio)phenols as well as small amounts of poly(hydrocarbylthio)phenols. It would be desirable to be able to convert at least a portion of these by-products to the more desirable 2-(hydrocarbylthio)phenols.

In other situations, it is desired to prepare another particular (hydrocarbylthio)phenol, e.g., a 4-(hydrocarbylthio)phenol; by-product (hydrocarbylthio)phenols are formed; and it would be desirable to convert at least a portion of those by-products to the desired (hydrocarbylthio)phenol.

SUMMARY OF INVENTION

An object of this invention is to provde a novel process for preparing (hydrocarbylthio)phenols.

Another object is to provide such a process wherein the (hydrocarbylthio)phenols are prepared by the redistribution of other (hydrocarbylthio)phenols.

These and other objects are attained by heating one or more (hydrocarbylthio)phenols selected from 2-, 3-, 4-, and poly(hydrocarbylthio)phenols in the presence of a catalytic amount of an aluminum phenoxide.

DETAILED DESCRIPTION (Hydrocarbylthio)phenols useful as starting materials in the practice of the invention are compounds having one or more hydrocarbylthio groups attached to an aromatic ring which optionally bears one more inert substituents in the positions unsubstituted by hydrocarbylthio groups. These (hydrocarbylthio)phenols are generally 4-(hydrocarbylthio)phenols, 3-(hydrocarbylthio)phenols, 2-(hydrocarbylthio)phenols, 2,4-di(hydrocarbylthio)phenols, 2,6-di(hydrocarbylthio)phenols and/or 2,4,6-tri(hydrocarbylthio)phenols.

As in McKinnie et al., the teachings of which are incorporated herein by reference, the hydrocarbylthio groups of the (hydrocarbylthio)phenols may be aliphatic, cycloaliphatic, or aromatic, such as methylthio, ethylthio, butylthio, cyclopentylthio, cyclohexylthio, benzylthio, p-tolylthio, p-chlorophenylthio, etc.; but they are preferably alkylthio groups, most preferably alkylthio groups containing 1–6 carbons.

The phenolic substrate of the (hydrocarbylthio)phenol may be a mono- or polynuclear hydroxy aromatic compound, optionally bearing inert substituents, such as the phenols taught in McKinnie, et al. and other such phenols. In general, these phenolic substrates are compounds containing one or more simple or fused aromatic rings, such as benzene, naphthalene, indene, benzofuran, biphenyl, etc., rings bearing one or more hydroxy substituents as well as any optional substituents on the same or different rings, including such compounds wherein two aromatic rings are linked by a divalent group, such as alkylidene, alkylene, oxygen, or sulfur linkage, e.g., bisphenol A, 4,4'-methylenediphenol, etc. However, the phenolic substrate is preferably a mononuclear, monohydroxy phenol, such as phenol itself, optionally bearing one or more alkyl side chains and up to two ar-chloro substituents. Thus, the preferred (hydrocarbylthio)phenol starting materials are optionally-substituted mononuclear, monohydroxy 2-, 3-, 4-, 2,4-, 2,6-, and/or 2,4,6-mono-, di-, and/or tri(alkylthio)phenols having 1–6 carbons in the alkyl groups.

As in McKinnie et al., the aluminum phenoxide can be prepared by contacting aluminum, an aluminum alkyl (e.g., triethylaluminum), or aluminum chloride with a phenol, desirably the (hydrocarbylthio)phenol starting material, at an elevated temperature, e.g. about 100°–200° C. The aluminum phenoxide syntheses taught in U.S. Pat. Nos. 2,831,898, 2,923,745, and 3,200,157 are also useful. In a preferred embodiment of the invention, the catalyst is formed in situ to form the phenoxide corresponding to the (hydrocarbylthio)phenol starting material.

The process of the invention is conducted by contacting the (hydrocarbylthio)phenol with a catalytic amount, e.g., about 0.01–0.5 mol per mol of (hydrocarbylthio)phenol, of the aluminum phenoxide or a precursor thereof and heating the reaction mixture at a suitable temperature, e.g., about 100°–300° C., until the hydrocarbylthio groups have been redistributed and the desired (hydrocarbylthio)phenol has been formed. If desired, the reaction can be conducted in the presence of an added phenol, such as phenol, p-cresol, etc., which can be useful in reacting with hydrocarbylthio groups of a poly(hydrocarbylthio)phenol when a (hydrocarbylthio)phenol containing fewer hydrocarbylthio groups is desired.

After completion of the redistribution reaction, the desired (hydrocarbylthio)phenol can be isolated by fractionation. Alternatively, the reaction mixture can be reacted with a suitable hydrocarbyl disulfide to provide additional quantities of the desired (hydrocarbylthio)phenol.

The following examples are given to illustrate the invention and are not intended as a limitation thereof.

EXAMPLE I

A suitable reaction vessel was charged, under nitrogen, with 3.1 g (0.022 mol) of pure 4-(methylthio)phenol that had been recrystallized from toluene and then with 0.20 ml (0.0015 mol) of triethylaluminum. The reaction was stirred at 170°–180° C. under nitrogen for about 18 hours. A sample of the reaction mixture was diluted with ether and extracted with 6N HCl and then saturated aqueous NaCl. Gas chromatographic analysis showed:

| Ingredient | Area % |
| --- | --- |
| Phenol | 23 |
| 2-(methylthio)phenol | 30 |
| 4-(methylthio)phenol | 11 |
| 3-(methylthio)phenol | 10 |
| 2,4-di(methylthio)phenol | 12 |
| 2,6-di(methylthio)phenol | 10 |
| 2,4,6-tri(methylthio)phenol | 2 |

| Ingredient | Area % |
| --- | --- |
| Others | 2 |

EXAMPLE II

In a nitrogen atmosphere, 0.3 ml (0.0022 mol) of triethylaluminum was added to 4.67 g (0.033 mol) of 2-(methylthio)phenol. The clear yellow solution was stirred at 170°–180° C. for 18.5 hours to give a clear cherry-red solution which was diluted with 10 ml of diethyl ether and extracted with 10 ml of 6N HCl and then with 10 ml of saturated aqueous NaCl. Gas chromatographic analysis of the sodium sulfate-dried organics indicated the following normalized composition:

| Ingredient | Area % |
| --- | --- |
| Phenol | 22 |
| 2-(methylthio)phenol | 34 |
| 4-(methylthio)phenol | 13 |
| 3-(methylthio)phenol | 3 |
| 2,4-di(methylthio)phenol | 14 |
| 2,6-di(methylthio)phenol | 9 |
| 2,4,6-tri(methylthio)phenol | 2 |
| Others | 2 |

EXAMPLE III

A suitable reaction vessel was charged with 4.0 g (0.020 mol) of 4-methyl-2,6-di(methylthio)phenol and 2.16 g (0.02 mol) of p-cresol, to which 0.18 ml (0.00135 mol) of triethylaluminum was added in a nitrogen atmosphere. The yellow solution was stirred at 160°–180° C. for 18 hours. After cooling, the reaction mixture was diluted with 10 ml of toluene, extracted with 10 ml 6N HCl and 10 ml saturated NaCl, dried over sodium sulfate, and filtered. Removal of the solvent with a rotary evaporator gave a reddish liquid which gas chromatographic analysis showed to contain:

| Ingredient | Area % |
| --- | --- |
| p-cresol | 19 |
| 4-methyl-2-(methylthio)phenol | 47 |
| 4-methyl-3-(methylthio)phenol | 4 |
| 4-methyl-2,6-di(methylthio)phenol | 29 |
| others | 1 |

Gas chromatographic analysis using dodecane as an internal standard showed that the product was 14% by weight of p-cresol, 40% by weight of 4-methyl-2-(methylthio)phenol, and 27% by weight of 4-methyl-2,6-di(methylthio)phenol.

It is obvious that many variations can be made in the products and processes set forth above without departing from the spirit and scope of this invention.

I claim:

1. A process which comprises heating one or more (hydrocarbylthio)phenols selected from 2-, 3-, 4-, and poly(hydrocarbylthio)phenols wherein the hydrocarbylthio groups are alkylthio, cycloalkylthio, or arylthio groups at a temperature of about 100°–300° C. in the presence of a catalytic amount of an aluminum phenoxide as the sole catalyst so as to redistribute the hydrocarbylthio groups on the phenolic substrate of the (hydrocarbylthio)phenol starting material.

2. The process of claim 1 wherein the starting (hydrocarbylthio)phenol is a 2-(hydrocarbylthio)phenol.

3. The process of claim 1 wherein the starting (hydrocarbylthio)phenol is a 4-(hydrocarbylthio)phenol.

4. The process of claim 1 wherein the starting (hydrocarbylthio)phenol is a mixture of (hydrocarbylthio)phenols.

5. The process of claim 1 wherein the (hydrocarbylthio)phenol is an (alkylthio)phenol.

6. The process of claim 5 wherein the (alkylthio)phenol is a mononuclear, monohydroxy(alkylthio)phenol having 1–6 carbons in the alkyl group.

7. The process of claim 6 wherein the (alkylthio)phenol is a (methylthio)phenol.

8. The process of claim 1 wherein the aluminum phenoxide is generated in situ.

* * * * *